(12) United States Patent
Kulesza

(10) Patent No.: US 9,561,164 B2
(45) Date of Patent: Feb. 7, 2017

(54) HIGH LUBRICATION SHAVING AID

(76) Inventor: John E. Kulesza, Wethersfield, CT (US)

( * ) Notice: Subject to any disclaimer, the term of this patent is extended or adjusted under 35 U.S.C. 154(b) by 0 days.

(21) Appl. No.: 13/882,403

(22) PCT Filed: Oct. 29, 2010

(86) PCT No.: PCT/US2010/054705
§ 371 (c)(1),
(2), (4) Date: Jul. 15, 2013

(87) PCT Pub. No.: WO2012/057782
PCT Pub. Date: May 3, 2012

(65) Prior Publication Data
US 2013/0287713 A1   Oct. 31, 2013

(51) Int. Cl.
*A61K 8/69* (2006.01)
*A61K 8/33* (2006.01)
*A61Q 9/02* (2006.01)

(52) U.S. Cl.
CPC . *A61K 8/33* (2013.01); *A61K 8/69* (2013.01); *A61Q 9/02* (2013.01); *Y10T 83/0405* (2015.04)

(58) Field of Classification Search
CPC ............... A61K 8/33; A61K 8/69; A61Q 9/02
USPC ...................... 424/59, 73; 514/164, 714, 722
See application file for complete search history.

(56) References Cited

U.S. PATENT DOCUMENTS

| | | | |
|---|---|---|---|
| 4,892,729 A * | 1/1990 | Cavazza | ........................ 424/73 |
| 5,204,093 A * | 4/1993 | Victor | .............................. 424/73 |
| 7,550,151 B2 | 6/2009 | Garrison | |
| 2003/0053980 A1 | 3/2003 | Dodd et al. | |
| 2004/0136916 A1* | 7/2004 | Garrison | ........................ 424/45 |
| 2005/0175563 A1* | 8/2005 | McNamara et al. | ......... 424/70.1 |
| 2008/0015295 A1 | 1/2008 | Williams et al. | |

* cited by examiner

*Primary Examiner* — Blessing M Fubara
(74) *Attorney, Agent, or Firm* — Dinsmore & Shohl LLP; Weston R. Gould

(57) ABSTRACT

A shaving aid composition is provided that includes an organic polyhalogenic agent that both promotes post application foaming and increases lubricity. The shaving aid is optionally used to deliver one or more therapeutics to the skin of a subject and is therefore operable to prevent or treat a skin condition.

18 Claims, No Drawings

HIGH LUBRICATION SHAVING AID

CROSS REFERENCE TO RELATED APPLICATION

This U.S. National Phase claims priority to PCT/US2010/054705, filed Oct. 29, 2010, the entire content of which is incorporated herein by reference.

FIELD OF THE INVENTION

The invention relates to removal of hair from the face or other body parts. More specifically, the invention relates to a shaving aid that provides improved lubrication and reduced irritation from shaving and does not rely on hydrocarbons for foaming. Therapeutics are optionally included to reduce sensitivity or treat skin conditions such as acne vulgaris and pseudofolliculitis barbae while shaving.

BACKGROUND OF THE INVENTION

Shaving commonly results in irritation to the site of razor drag. This irritation is worsened by use of dull razor blades commonly causing a user to press the blade harder to the skin. Shaving creams are designed to provide a soothing affect by adding moisture to the shaved area and lubricate the interface between the blades and the skin.

Of the three types of shaving creams, lathering creams are the most common. The lathering properties of these shaving creams are formed by mixing 1 part stearic acid to 3 parts oil such as coconut oil. Fatty acid saponification is typically achieved by also combining sodium hydroxide or potassium hydroxide yielding glycerol and a soap. As much as 30% to 50% of the shaving cream composition may be soap.

The conventional shaving creams tend to have relatively high pH values that can produce skin irritation. The non-lathering shaving creams or gels are simple oil-water emulsions that provide lower pH due to the absence of metal hydroxides. The non-lathering properties, however, typically fail to provide the depth and appearance of the foaming creams which in turn decreases identifiability of yet to be shaved regions.

Finally, post foaming gels produce foam upon gentle agitation after or during application to the skin. Prior art post foaming gels are typically simple aqueous dispersions. The foaming action is due to vaporization of aliphatic hydrocarbons during application. Storage of these aliphatic hydrocarbon requiring post-foaming gels requires pressurization to prevent volatilizing the aliphatic hydrocarbons.

The use of volatile hydrocarbons to promote foaming in post-foaming gels and other shaving creams reduces the lubricity of the final product on the skin. In addition, these foaming aids are linked to global warming. Thus, there is a need for a foaming shaving cream that does not require hydrocarbons for foaming and provides improved lubricity.

SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

A shaving aid composition is provided that does not rely on volatile saturated aliphatic hydrocarbons for foaming such that it is optionally free of saturated aliphatic hydrocarbon and does not require storage under pressure. A shaving aid composition includes an organic polyhalogenic post-foaming agent that induces foaming and unexpectedly increases lubricity. A shaving aid also includes a hydrophilic surfactant, illustratively triethanolamine stearate, at 5-20 percent by weight, and water from 35 to 80 percent by weight. The organic polyhalogenic post-foaming agent is optionally present at 1 to 30 percent by weight of the total composition. In some embodiments the organic polyhalogenic post-foaming agent is present from 3 to 10 percent by weight, optionally from 3 to 7 percent by weight, optionally 5 percent by weight. Exemplary organic polyhalogenic post-foaming agents include methoxynonafluorobutane or ethoxynonafluorobutane.

One or more therapeutics are optionally included in a shaving aid composition. A therapeutic is optionally: vitamin A or its derivatives; keratolitic agents such as hydroxy acids; benzoyl peroxide; antimicrobials; anti-neoplastic agents; anti-viral agents; steroidal or non-steroidal anti-inflammatory agents; UV filters; antioxidants; lipids; hair growth inhibitors such as eflornithine; or immunomodulators. In some embodiments, a first therapeutic is provided along with a second therapeutic. A first therapeutic is optionally vitamin A or its derivatives, a hydroxy acid, benzoyl peroxide, or an antimicrobial.

A shaving aid optionally includes one or more additives such as a lubricant, preservative, emulsifier, foam booster or enhancer, thickener, solvent, skin conditioner, humectant, color, fragrance antioxidant, chelator, natural extract, vitamin, UV light filtering agent, opacifying agent, solvent, styling polymer, anti-static agent, anti-dandruff aid, pediculocides, or combinations thereof. One or more emollients are optionally included. An emollient is optionally present from 0.1 to 8.0 percent by weight of the composition.

A process of treating a skin condition in a subject is also provided whereby a shaving aid composition is applied to the skin of a subject and subsequently removed from the skin. Removal of a shaving aid composition is optionally by rinsing, a straight edge razor, or by wiping with a substrate such as a cloth. The shaving aid is optionally incubated on the skin of a subject for between 20 seconds to 2 minutes. In some embodiments the foaming time of a shaving aid composition signals sufficient time for therapeutic application.

DETAILED DESCRIPTION OF THE PREFERRED EMBODIMENTS

The following description of the preferred embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only.

A saturated hydrocarbon free, post-application foaming shaving aid is provided that employs novel volatile agents that produce foaming after application to the skin and simultaneously improve lubricity and reduce skin irritation. The invention has utility as a composition for improved shaving or for delivery of a therapeutic to the skin of a subject.

A shaving aid is a form of post-application foaming gel that incorporates an organic polyhalogenic post-foaming agent that promotes both foaming and lubricity. The term "post-application foaming" means that the composition will continue to foam for a foaming time subsequent to application to the skin in the presence or absence of additional agitation. It was unexpectedly discovered that an organic polyhalogenic post-foaming agent possess the proper volatility to induce foam generation during and following initial application and also increases lubricity, thus, reducing razor friction and providing visual feedback of a shaved location.

A shaving aid composition illustratively includes one or more hydrophilic surfactants, one or more organic polyhalogenic post-foaming agents, and water. A hydrophilic surfactant can be a salt of a higher fatty acid. Hydrophilic surfactants are well known in the art and may be purchased or prepared in any conventional manner. For example, hydrophilic surfactants are optionally prepared by reacting a basic material such as triethanolamine or alkali hydroxides directly with a fatty acid such as a saturated or unsaturated fatty acid which is optionally, but not limited to a $C_{10}$ to $C_{22}$ containing molecule. A fatty acid optionally includes longer or shorter hydrocarbon chains, unsaturated linkages, or other derivatives of a fatty acid. Combinations of multiple fatty acids are similarly operable. Illustrative examples of hydrophilic surfactants illustratively include stearate and palmitate soaps or derivatives thereof, such as soluble amine salts of stearic and palmitic acid. Triethanolamine stearate is used as a hydrophilic surfactant in particular embodiments of a shaving aid composition. Hydrophilic surfactants are optionally employed in amounts from 5% to 20% by weight of the total composition.

It is well known that the commercial product known as stearic acid is actually a mixture consisting primarily of stearic and palmitic acids. Therefore, it is recognized that a hydrophilic surfactant is optionally a mixture of one or more hydrophilic surfactants, although hydrophilic surfactants of chemically pure fatty acids work equally well for the purposes of the inventions. Optionally, palmitic acid available under the trademark "Emersol" is used in the present invention. In some embodiments, the palmitic acid used is sold under the trademark "Emersol-140 (3:1)" which is a blend of palmitic acid and stearic acid in a 3:1 ratio.

A hydrophilic surfactant is optionally made by the combination of triethanolamine (triethanolamine) and stearic acid to form TEA-stearate. TEA-stearate is a salt formed by the combination of triethanolamine and stearic acid. When triethanolamine present in a water phase solution is combined with stearic acid present in an oil phase solution, TEA-stearate is formed in situ during manufacture of a shaving aid composition.

A shaving aid composition provides both a post-application foaming as well as an unexpectedly increased level of lubricity. Among the nearly infinite possibilities of agents that could function to provide post-application foaming characteristics to a shaving aid, it was unexpectedly discovered that organic polyhalogenic agents not only have the proper volatility to promote foaming after application to the skin, but also provide significantly enhanced lubrication. Without being limited to one particular theory, it is believed that the enhanced lubricity is due to a sufficient level of agent remaining in the composition during the time required for composition removal such as during normal shaving. This discovery is particularly interesting due to the significant oil-like properties of many organic polyhalogenic agents that are unlike the normal volatile saturated hydrocarbons commonly used in shave gels which are totally void of lubricant properties. The organic polyhalogenic agents can be emulsified like oils yet are volatile enough to promote foaming after application to the skin. Additionally, the art considers organic polyhalogenic agents such as methoxynonafluorobutane, sold under the tradename CF-61, to be an alcohol replacement. The surprising ability of the organic polyhalogenic agents to be used in an emulsion for a shaving aid composition is entirely unexpected since molecules that are alcohols or possess alcohol-like properties actually destroy emulsions and would prevent the shaving aid from foaming at all.

Organic polyhalogenic agents are optionally those disclosed in U.S. Pat. No. 6,251,375, the contents of which are incorporated herein by reference. In particular instances, agents incorporate a halogen such as one or more fluorine atoms. In some specific instances, an agent is a perfluoro ether. In some particular instances, an agent is methoxynonafluorobutane (CF-61) or ethoxynonafluorobutane (CF-76) available from 3M Specialty Materials, St. Paul, Minn.

An agent has a boiling point that characterizes volatility sufficient to induce foaming optionally within 90 seconds after application to the skin. In some embodiments, significant foaming is observed within 120, 90, 60, 50, 40, 30, or 20 seconds following application to the skin which may or may not require stimulation by gentle agitation such as by rubbing. An organic polyhalogenic agent optionally has a boiling point less than 78° C. Optionally, an agent has a boiling point between 35° C. and 70° C. An organic polyhalogenic agent is optionally present at a final concentration of 1 percent to 30 percent by weight of the composition. Optionally, an organic polyhalogenic agent is present at from 3 percent to 10 by weight of the composition. Optionally, an organic polyhalogenic agent is present between 3 and 7 by weight of the composition. In some embodiments the organic polyhalogenic agent is present at 5 percent by weight of the composition. It is appreciated that more than one organic polyhalogenic agent is optionally present in an inventive composition.

In some embodiments, 2, 3, 4, 5, 6, or more organic polyhalogenic agents are present in a shaving aid composition. When more than one organic polyhalogenic agent is present the agents optionally have boiling points within 10° C. or each other. Optionally, a first organic polyhalogenic agent promotes foaming more readily than a second organic polyhalogenic agent due to a lower boiling point of a first polyhalogenic agent.

The presence of an organic polyhalogenic agent eliminates the need for a saturated hydrocarbon normally used as a volatile agent to induce foaming such as n-butane or n-pentane. As such, a shaving aid composition optionally is free of saturated hydrocarbon.

A shaving aid composition includes water. Water is optionally present from 35 and 80 percent by weight of the composition. The water is optionally purified so as to remove contaminants such as solids and other microorganisms, or subjected to processes to remove contaminating ions. Illustratively, compositions include deionized water prepared by methods and using apparatuses known in the art. Methods of purifying or filtering water are well known in the art.

A shaving aid composition optionally includes a therapeutic operable to treat one or more skin or systemic conditions of a subject. Skin or systemic conditions treatable with the shaving aid illustratively including pseudofolliculitis barbae, acne, wrinkles, dryness, eczema, and psoriasis, among others. U.S. Pat. No. 3,932,665 describes retinal as a therapeutic agent in a method for treating acne by topical application. The disclosure of U.S. Pat. No. 3,932,665 is accordingly hereby incorporated by reference. The application of a therapeutic to treat acne vulgaris or pseudofolliculitis barbae in humans is described in U.S. Pat. No. 5,204,093, the contents of which are incorporated herein by reference.

As used herein the term "therapeutic" refers to a molecule suitable for delivery to the skin or mucosal regions of a subject. Optionally, a therapeutic has pharmaceutical activity and is present for the treatment or prevention of a skin condition. Examples of therapeutics illustratively include: vitamin A or its derivatives; hydroxy acids; aromatic molecules such as benzoyl peroxide; antimicrobials such as antiseptic agents, the antibiotics illustratively tea tree oil, resorcinol, triclosan (5-chloro-2-(2,4-dichlorophenoxy)phenol), azelaic acid, erythromycin, sodium sulfacetamide, tetracycline and derivatives, and clindamycin; anti-viral agents illustratively ganciclovir, trifluorothymidine, and related compounds; steroidal or non-steroidal anti-inflammatory agents illustratively flurbiprofen, ibuprofen, naproxen, indomethacin, hydrocortisone, and other anti-inflammatory compounds; ultraviolet light (UV) filters illustratively benzophenone derivatives such as oxybenzone, octocrylene, octyl methoxycinnamate, and avobenzone; radiation proactive agents illustratively methyluracils such as 6-methyluracil and 4-methyluracil; and immunomodulating molecules such as imiquimod, tacrolimus, and pimecrolimus. It is appreciated that a shaving aid composition optionally includes more than one therapeutic. Optionally, 2, 3, 4, 5, 6, or more therapeutics are present in a shaving aid composition. A therapeutic is optionally a prodrug that is converted to a desired active species optionally in the skin or layer thereof. For considerations in synthesizing and using prodrugs see Prodrugs: Challenges and Rewards, 2007, Stella, V, et al. eds, Springer Science and Business Media, LLC, New York, the entire contents of which are incorporated herein by reference. Concentrations and dosing of a therapeutic are readily determined by one of ordinary skill in the art.

As an illustrative example, a therapeutic is benzoyl peroxide. Benzoyl peroxide, $(C_6H_5CO)_2O_2$, is a crystalline solid which is generally stable at room temperature. Typical vehicles used in the topical application of benzoyl peroxide include creams, lotions and gels. For example, U.S. Pat. No. 4,778,674, incorporated herein by reference, discloses a dry aerosol foam containing benzoyl peroxide for use in the treatment of acne vulgaris. Benzyol peroxide is equally suitable for delivery to the skin of a subject in a shaving aid composition. Benzyol peroxide is included in some embodiments of a shaving aid composition at concentrations of 10% or less, optionally, 5% or less, optionally, 2.5% or less each by weight of the total composition.

In addition to acne, other serious skin conditions treatable or preventable with a shaving aid as described herein include pseudofolliculitis barbae, pseudofolliculitis of the beard, or pseudofolliculitis capitae, all more commonly known as "razor bumps." These conditions typically occur on the human neck, jowl and chin as a response to ingrown hairs that occur after shaving and are particularly severe in subjects with curly hair. These conditions and are characterized by erythematous lesions, firm papules, pustules, or cysts which contain buried hairs. A shaving aid composition is capable of promoting alleviation or prevention of such skin conditions by the enhanced lubricity provided by the organic polyhalogenic agent that prevents razor drag and irritation. In addition, a therapeutic is optionally included that serves to regulate the physiological response to an ingrown hair.

Multiple therapeutics are optionally present in a shaving aid composition. In some embodiments the therapeutics salicylic acid, triclosan, and tea tree oil are included optionally for the prevention or treatment of pseudofolliculitis barbae, pseudofolliculitis of the beard, or pseudofolliculitis capitae. Salicylic acid is optionally present at concentrations of 2% or less by weight. In some embodiments salicylic acid is present at 1% by weight or less. Optionally, salicylic acid is present at 0.5% by weight. Triclosan is an antimicrobial due to its action as an antibacterial and antifungal aid and thus is similarly operable as a preservative. Triclosan is optionally present in a shaving aid composition at 2.5 percent by weight or less, optionally at 0.5 percent. Tea tree oil from leaves of the *Melaleuca alternifolia* possesses antimicrobial and antiseptic properties due to antibacterial, antifungal, and antiviral actions. Tea tree oil is optionally present at 2.5% or less by weight. Optionally, tea tree oil is present at 0.5% by weight.

As used herein a "subject" is defined as any organism that could benefit from topical application of a shaving aid composition. A subject illustratively includes mammals that are illustratively humans, non-human primates, horses, goats, cows, sheep, pigs, dogs, cats, and rodents.

A shaving aid optionally includes one or more additives. An additive is optionally a lubricant, preservative, emulsifier, foam booster or enhancer, thickener, solvent, skin conditioner, humectant, color, fragrance, antioxidant, chelator, natural extract, vitamin, UV light filtering agent, opacifying agent, solvent, styling polymer, anti-static agent, anti-dandruff aid, pediculocide, or combinations thereof. The levels of an additive are readily determinable to one of ordinary skill in the art. Illustratively, some embodiments contain tea tree oil, which alone possess an unpleasant odor. Relatively lower amounts of lavender oil (illustratively, 0.3% lavender oil to 0.5% tea tree oil) balance this odor and provide a fresh, pleasing scent to the composition.

While the organic polyhalogenic agent is sufficient to provide increased lubricity, a shaving aid composition optionally includes one or more additional lubricants. Lubricants are typically included in a shaving aid composition to increase lubrication of the area to be shaved so that the razor will travel with as little resistance as possible. A lubricant is optionally of sufficiently low volatility such that it remains in the shaving aid composition during normal shaving times—illustratively 10 minutes to 1 minute, or any value of range therebetween. As such, a lubricant is optionally described as a non-volatile lubricant. Lubricants illustratively include: water soluble polymers, illustratively poly (ethylene oxide) polymers (e.g. POLYOX) and cellulosic polymers (e.g. hydroxyethyl cellulose); mineral oil; lauroyl lysine such as that sold under the tradename Amihope LL from Ajinomoto, Fort Lee, N.J.; long chain fatty acid esters; and other water soluble or non-water soluble lubricants recognized in the art.

One or more emulsifiers are optionally included in a shaving aid composition. An emulsifier is optionally included to enhance emulsification of an organic polyhalogenic agent or other component of a shaving aid composition. An example of a type of emulsifier is a surfactant. Illustrative examples of emulsifiers include proteins such as soy or other lechtins, dimethicone copolyol, propylene glycol stearate, sorbitan tristearate, sorbitan monooleate, sorbitan trioleate, emulsifying wax, cetearyl alcohol, polysorbate 20, and ceteareth 20, among others known in the art.

A shaving aid composition optionally includes one or more foam enhancers. A foam enhancer serves to increase the time that foaming is observed. Illustrative examples of foam enhancers include povidone (PVP), and dimethicone copolyol, among others known in the art. The level of foam enhancer is readily determined by one of ordinary skill in the art. In some embodiments providone is used as a foam enhancer at levels of 2.0 percent by weight or less, optionally at 0.1 percent by weight.

One or more solvents are optionally included in a shaving aid. A solvent is optionally provided to solubilize one or more components of a shaving aid composition during its manufacture. Illustratively, propylene glycol is used to solubilize one or more therapeutics for enhanced incorporation into a shaving aid.

In some embodiments a thickener is added to increase the resistance to deformation of a shaving aid composition. Illustrative examples of a thickener include cetyl alcohol, sodium alginate, proteins such as lechtins and collagens, sorbitol, and gelatin, among others known in the art. In some embodiments, cetyl alcohol is present at 2% by weight or less, optionally at 1% by weight.

A shaving aid composition optionally includes an emollient to soften and soothe the skin. Suitable emollients are known to those skilled in the art and illustratively include non-volatile hydrocarbons, silicones, fatty alcohols, fatty acids, synthetic or natural esters, and combinations thereof, among others known in the art. Specific illustrative examples of emollients include lanolin, cetyl alcohol, and stearyl alcohol. Suitable emollients can be included in an amount between about 0.1% to about 8.0%, optionally in an amount ranging from about 0.5% to about 6.0%, optionally from about 1.0% to about 5.0% by weight.

Humectants generally promote the retention of water and are desirable in a shaving aid composition. Humectants illustratively include proplyene glycol, sorbitol, glycerol, glycerin, hyaluronic acid, sodium hyaluronate, other humectants known in the art, or combinations thereof.

A process of treating a skin condition is also provided wherein the process includes applying to the skin of a subject a shaving aid composition that includes one or more hydrophilic surfactants at 5-20 percent by weight, one or more organic polyhalogenic post-foaming agents, water from 35 to 80 percent by weight, and one or more therapeutics and subsequently removing the shaving aid from the skin.

The shaving aid remains on the skin for a sufficient time to allow therapeutic contact of a therapeutic contained therein with the skin. This may include the time during which a shaving aid is agitated. In some embodiments, a shaving aid is physically agitated for a foaming time on the skin during application and for as much as two minutes thereafter. Optionally, the shaving aid is agitated from 10 seconds to 120 seconds, optionally from 30 seconds to 60 seconds. It is appreciated that the shaving aid is optionally agitated for any time less than two minutes e.g. 120, 110, 100, 90, 80, 70, 60, 50, 40, 30, 20, or 10 seconds. It is appreciated that the foaming time of a shaving aid is optionally indicative of a sufficient amount of time for the shaving aid to remain on the skin. Optionally, the foaming time combined with normal shaving time, typically anywhere from 10 minutes to 1 minute, is sufficient time for a therapeutic to contact the skin of a subject. Thus, a shaving aid is operable to treat or prevent a disease or condition while simultaneously supporting a normal, optionally daily, activity of shaving.

In some embodiments, a shaving aid composition is applied following a pre-treatment to the skin. A pre-treatment illustratively includes subjecting the skin to heat such as by contact with a hot compress, a hot towel, or placing the skin in a steam environment such as a shower, or other steam producing area or mechanism.

Removal of the shaving aid composition is optionally by rinsing or by removal with a razor, illustratively a straight edge razor. Razors are any type of razor operable for shaving any area of the body. Single or multiple blade razors where the blades are straight or curved are operable for removing a shaving aid composition from the skin. Sources of these and other razors are well known in the art.

While the shaving aid is typically used for promoting improved shaving, its application to the skin need not be used as such. Optionally, a subject can apply a shaving aid composition to the skin and remove it such as by rinsing with water or simply by wiping off excess shaving aid composition by wiping with a substrate such as a towel or other material.

A shaving aid is typically packaged into an air free delivery container. Suitable air free delivery containers are known in the art and illustratively include an airless pump. While a shaving aid composition does not require storage under more than atmospheric pressure, with inert gasses, or using other common precautions, exposure to air immediately induces foaming of the shaving aid composition. This, storage or delivery in an air free environment is desirable.

Various aspects of the present invention are illustrated by the following non-limiting examples. The examples are for illustrative purposes and are not a limitation on any practice of the present invention. It will be understood that variations and modifications can be made without departing from the spirit and scope of the invention. While the examples are generally directed to shaving aids including therapeutics directed to prevention or treatment of pseudofolliculitis barbae or acne, it is appreciated that other therapeutics for prevention or treatment of other conditions are similarly operable in a shaving aid composition. A person of ordinary skill in the art readily understands where such necessary or optional reagents, compounds, or ingredients may be obtained.

Example 1

Shaving aid compositions with different levels of methoxynonafluorobutane or ethoxynonafluorobutane as exemplary organic polyhalogenic agents are provided in Table 1. Formulation 1A serves as a control composition. Percentages are expressed as percent by weight of the total composition. QS represents the level of water necessary to achieve 100 weight percent total.

TABLE 1

| Weight percent | Formulation | | | |
| --- | --- | --- | --- | --- |
| | 1A % | 1B % | 1C % | 2A % |
| Water | qs | qs | qs | qs |
| Dimethicone copolyol | 1 | 1 | 1 | 1 |
| Triethanolamine | 2 | 2 | 2 | 2 |
| Stearic acid | 12.5 | 12.5 | 12.5 | 12.5 |
| Mineral oil | 3.25 | 3.25 | 3.25 | 3.25 |
| Propylene glycol stearate | 3 | 3 | 3 | 3 |
| Cetyl alcohol | 1 | 1 | 1 | 1 |
| Polyethylene | 0.75 | 0.75 | 0.75 | 0.75 |
| Methoxyonafluorobutane | 0 | 5 | 10 | 0 |
| Ethoxyonafluorobutane | 0 | 0 | 0 | 5 |
| Lauryl lysine | 0.5 | 0.5 | 0.5 | 0.5 |
| Propylene glycol | 6.5 | 6.5 | 6.5 | 6.5 |
| Salicylic acid | 0.5 | 0.5 | 0.5 | 0.5 |
| Triclosan | 0.5 | 0.5 | 0.5 | 0.5 |
| Tea Tree oil | 0.5 | 0.5 | 0.5 | 0.5 |
| Lavender oil | 0.3 | 0.3 | 0.3 | 0.3 |

TABLE 1-continued

| Weight percent | Formulation | | | |
|---|---|---|---|---|
| | 1A % | 1B % | 1C % | 2A % |
| Povidone | 0.1 | 0.1 | 0.1 | 0.1 |
| PEG 14-M | 0.1 | 0.1 | 0.1 | 0.1 |

Preparation of exemplary shaving aids is accomplished by forming a water phase solution, forming an oil phase solution, combining the water phase solution and oil phase solution to form a TEA-stearate containing emulsion, combining methoxynonafluorobutane or ethoxynonafluorobutane with the emulsion, and adding a glycol-phase solution.

A water phase solution is formed by combining an appropriate amount of DI water with dimethicone copolyol and trolaime to a final weight percent of 1.9. A small level of triethanolamine (0.1% by weight) is reserved for addition at a later step to enhance solubilization of a therapeutic. The water phase components are vigorously agitated by propeller mixing at atmospheric pressure at 70° C.

In a separate container an oil phase solution is formed by combining stearic acid, mineral oil, propylene glycol, cetyl alcohol, and polyethylene in a single container and heating to 70° C. with gentle mixing.

While maintaining temperature at 70° C., the oil phase solution and the water-phase solution are combined to create an oil in water emulsion using TEA-stearate. The emulsion is allowed to cool to 35° C. A mixture of either methoxynonafluorobutane or ethoxynonafluorobutane combined with lauroyl lysine is then combined with the emulsion. The solution is homogenized.

A glycol phase solution is formed that includes propylene glycol, salicylic acid, triclosan, tea tree oil, lavender oil, povidone, and PEG 14M by gentle mixing at ambient temperature. The glycol phase solution is then added to the organic polyhalogenic containing emulsion and the resultant product is mixed and cooled to a set point of 30° C.

The resulting product is placed in an airless pump and stored at ambient temperature until use.

Example 2

A second process is used to formulate shaving aids of the following composition:

TABLE 2

| Weight percent | Formulation | |
|---|---|---|
| | 3A % | 3B % |
| Water Phase | | |
| Water | qs | qs |
| Acrylates copolymer | 2 | 2 |
| Dimethicone copolyol | 1 | 1 |
| PEG-14M | 0.1 | 0.1 |
| Triethanolamine | 1 | 1 |
| Oil Phase | | |
| Stearic acid | 12.5 | 12.5 |
| Mineral oil | 3.25 | 3.25 |
| Propylene glycol stearate | 3 | 3 |
| Cetyl alcohol | 1 | 1 |
| Polyethylene | 0.75 | 0.75 |
| Glycol Phase | | |

TABLE 2-continued

| Weight percent | Formulation | |
|---|---|---|
| | 3A % | 3B % |
| Propylene glycol | 6.5 | 6.5 |
| Salicylic acid | 0.5 | 0.5 |
| Triclosan | 0.5 | 0.5 |
| Triethanolamine | 0.5 | 0.5 |
| Post-foaming Agent Solution | | |
| Methoxyonafluorobutane | 5 | 0 |
| Ethoxyonafluorobutane | 0 | 5 |
| Lauryl lysine | 0.5 | 0.5 |
| Tea Tree oil | 0.5 | 0.5 |
| Lavender oil | 0.3 | 0.3 |

An alternate preparation method is accomplished by forming a water phase solution, forming an oil phase solution, combining the water phase solution and oil phase solution to form a TEA-stearate containing emulsion, preparing a glycol-phase solution, combining the glycol phase solution with the emulsion, forming a post-foaming agent solution, and combining the post-foaming agent solution with the emulsion.

A water phase solution is formed by combining an appropriate amount of DI water with acrylates copolymer, dimethicone copolyol, PEG-14M, and triethanolamine each to the final shaving aid weight percentages as found in Table 2. The water phase components are vigorously agitated by propeller mixing at atmospheric pressure at 70° C.

In a separate container, an oil phase solution is formed by combining stearic acid, mineral oil, propylene glycol stearate, cetyl alcohol, and polyethylene each to the final shaving aid weight percentages as found in Table 2 in a single container and heating to 70° C. with gentle mixing.

While maintaining temperature at 70° C., the oil phase solution and the water phase solution are combined to create an oil-in-water emulsion using TEA-stearate. The emulsion is allowed to cool to 60° C.

A glycol phase solution is prepared by combining propylene glycol, salicylic acid, triclosan, and triethanolamine each to the final shaving aid weight percentages as found in Table 2 in a single container with mixing and heated to 60° C. The glycol phase solution is then added to the emulsion at 60° C. The emulsion is then cooled to 42° C.

A post-foaming agent solution is prepared by combining an organic polyhalogenic agent with tea tree oil, lauroyl lysine and lavender oil at the final weight percentages of Table 2 with gentle mixing at ambient temperature. The post-foaming agent solution is then combined with the emulsion.

The resulting solution is homogenized, then mixed and cooled to a set point of 30° C.

The resulting product is placed in an airless pump and stored at ambient temperature until use.

Example 3

Foaming times are determined by application of the shaving aids of Examples 1 and 2 to a surface and monitoring the time of color change to a white foamy substance. The control formulation 1A did not show significant foaming upon measuring for up to 10 minutes. The formulations containing methoxynonafluorobutane (both 1B, 1C, and 3A) begin foaming within 5 seconds of application, and reach a full opaque white foamy substance within 30 seconds that is further enhanced out to 90 seconds. Formulation 2A shows initial foaming at 5 seconds followed by full foaming at 2 minutes.

Example 4

The presence of an organic polyhalogenic agent increases lubricity. Skin friction tests following application of the shaving aids of Examples 1 and 2 are performed essentially as described in U.S. Pat. Pub. No. 2009/0053158, the contents of which are incorporated herein by reference. The skin friction meter made by Measurement Technologies (Cincinnati, Ohio) is available through Aca-Derm, Inc of Menlo Park, Calif. is employed whereby a probe is pressed against a synthetic skin surface and measures the force required to either push or pull a probe on the surface. The skin friction meter measures the coefficient of friction for each tested sample.

Friction measurements are made following application of either no shaving aid or the formulations of Examples 1 and 2 onto synthetic skin ("VITRO-SKIN," IMS Inc. (Orange, Conn.)). The synthetic skin is cut into 2×2 cm squares and placed in a hydration chamber according to the manufacturer's direction. Baseline readings are made prior to application of a shaving aid composition. The formulations of Examples 1 and 2 as well as a commercially available shave gel sold as Edge Sensitive Skin Shave Gel™ (10 μl) are individually applied to the test skin using a micropipette and allowed to dry for 15 seconds. The probe is then placed on the site and measurements are taken following 30 and 90 seconds of foaming time. In some tests the shaving aids are applied to the surface with gentle agitation for the 30 and 90 second foaming time to enhance foaming prior to assessing lubricity. The latter value corresponds to an extended shaving process. Each formulation is tested in triplicate, and the average results are presented in Table 3 as friction meter units.

TABLE 3

| Formulation | Baseline | 30 sec | % change | 90 sec | % change |
|---|---|---|---|---|---|
| 1A | 6.1 | 3.7 | −39 | 3.8 | −38 |
| 1B | 5.9 | 2.4 | −59 | 2.4 | −59 |
| 1C | 6.0 | 2.6 | −57 | 3.0 | −50 |
| Edge Sensitive Skin Shave Gel | 6.0 | 3.9 | −35 | 4.3 | −28 |

The inclusion of methoxynonafluorobutane or ethoxynonafluorobutane produces a significant reduction in skin friction over the same formula that did not include an organic polyhalogenic compound (1A) and a popular commercially-available shaving product claiming reduced friction. Formulation 1C with a 10% concentration of methoxynonafluorobutane causes viscosity changes in the test emulsion that result in slightly more skin friction. Similar overall results are obtained with ethoxynonafluorobutane.

Example 5

The formulations of Examples 1 and 2 are compared in a study of human subjects presenting with pseudofolliculitis barbae. 90 male subjects aged 18 to 35 are divided into equal sized groups at random and tested for reversal of pseudofolliculitis barbae by shaving with the shaving aids of Examples 1 or 2 for two weeks. Skin testing is performed essentially as described in U.S. Pat. No. 5,204,093, incorporated herein by reference. Each subject's face is washed with warm water and a non-medicated mild soap. The face is then rinsed. A thin layer of shaving aid is evenly applied to the face and allowed to foam for 30 seconds with no agitation. In some tests, subjects agitated the shaving aid following initial application for 60 seconds prior to shaving. Each subject then shaves using a straight edge razor in a normal manner. Upon completion of the shaving, the face is rinsed with cool water.

The subjects in the control group using control formulation 1A show mildly reduced levels of pseudofolliculitis barbae compared to prior to testing as determined by a clinical dermatologist. The subjects in test groups using formulations 1B, 1C, 2A, 3A, and 3B each show significantly greater improvement compared to the control group.

Example 6

Inclusion of benzoyl peroxide to a final concentration of 5 percent by weight in the formulations of Examples 1 or 2 reduce skin conditions in human subjects. Skin testing is performed by the method of Example 5. Briefly, twenty male caucasians aged 16 to 35 with acne vulgaris and twenty males of the black race with pseudofolliculitis barbae are placed in respective test groups. Each individual is shaved daily with the benzoyl peroxide containing shaving aids of Formulas 1A, 1B, 2A, 3A, and 3B using the shaving methods of Example 5.

All subjects note a clinical improvement in their respective condition within 2-3 days. A clinical evaluation by a dermatologist, after one week of treatment using the shaving aid composition reveals an improvement of 80-90% in the initial condition of the subject's skin. A more pronounced affect is observed in the treatment group with pseudofolliculitis barbae relative to formulation 1A due to the improved lubricity provided by the organic polyhalogenic agent.

Various modifications of the present invention, in addition to those shown and described herein, will be apparent to those skilled in the art of the above description. Such modifications are also intended to fall within the scope of the appended claims.

It is appreciated that all reagents are obtainable by sources known in the art unless otherwise specified.

Patents and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A post-application foaming shaving aid composition comprising:
   triethanolamine stearate;
   methoxynonafluorobutane;
   polyethylene;
   lauroyl lysine; and
   water from 35 to 80 percent by weight;
   said composition free of saturated aliphatic hydrocarbons.

2. The composition of claim 1 wherein said methoxynonafluorobutane is present at 1 to 30 percent by weight of the total composition.

3. The composition of claim 1 wherein said methoxynonafluorobutane is present at 3 to 10 percent by weight.

4. The composition of claim 1 wherein said methoxynonafluorobutane is present at 3 to 7 percent by weight.

5. The composition of claim 1 further comprising a therapeutic.

6. The composition of claim 5 wherein said therapeutic is vitamin A or its derivatives; hydroxy acids; benzoyl peroxide; antimicrobials; anti-viral agents; nonsteroidal anti-inflammatory agents; UV filters; lipids; or immunomodulators.

7. The composition of claim 1 further comprising an additive.

8. The composition of claim 7 wherein said additive is a preservative, emulsifier, foam booster or enhancer, thickener, solvent, skin conditioner, humectant, color, fragrance, antioxidant, chelator, natural extract, vitamin, UV light filtering agent, opacifying agent, solvent, styling polymer, anti-static agent, anti-dandruff aid, pediculocide, or combinations thereof.

9. The composition of claim 1 further comprising an emollient, said emollient present from 0.1 to 8.0 percent by weight of the composition.

10. A post-application foaming shaving aid composition comprising:
    triethanolamine stearate;
    methoxynonafluorobutane and ethoxynonafluorobutane at 1 to 10 percent by weight;
    water from 35 to 80 percent by weight;
    a first therapeutic;
    polyethylene; and
    lauroyl lysine;
    said composition free of saturated aliphatic hydrocarbons.

11. The composition of claim 10 wherein said first therapeutic is an antimicrobial therapeutic.

12. The composition of claim 10 further comprising a second therapeutic.

13. The composition of claim 10 wherein said first therapeutic is a: vitamin A or its derivatives; hydroxy acid; benzoyl peroxide; or an antimicrobial.

14. A process of treating a skin condition in a subject comprising:
    applying to the skin of a subject a therapeutic composition of claim 10;
    and
    removing said composition from skin.

15. The process of claim 14 wherein said removing is by rinsing or removal with a straight edge razor.

16. The process of claim 14 wherein said therapeutic is a vitamin A or its derivatives; hydroxy acid; benzoyl peroxide; resorcinol; antimicrobial; anti-neoplastic agent; anti-viral agent; anti-inflammatory agent; UV filter; lipid; immunomodulators; or combinations thereof.

17. The process of claim 14 wherein said therapeutic is benzoyl peroxide, salicylic acid, an antimicrobial, or a retinol.

18. The process of claim 14 further comprising incubating or agitating said shaving aid on said skin for between 20 seconds and 2 minutes prior to said removing.

* * * * *